US011051826B2

(12) United States Patent
Baldwin et al.

(10) Patent No.: US 11,051,826 B2
(45) Date of Patent: Jul. 6, 2021

(54) EMBOLIC COMPOSITIONS

(71) Applicant: MicroVention, Inc., Aliso Viejo, CA (US)

(72) Inventors: Aaron Baldwin, Aliso Viejo, CA (US); Ami Mehta, Aliso Viejo, CA (US); Jonathan Lam, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 16/442,869

(22) Filed: Jun. 17, 2019

(65) Prior Publication Data

US 2019/0298388 A1  Oct. 3, 2019

Related U.S. Application Data

(63) Continuation of application No. 15/687,263, filed on Aug. 25, 2017, now Pat. No. 10,368,874.

(60) Provisional application No. 62/380,317, filed on Aug. 26, 2016.

(51) Int. Cl.

| *A61B 17/12* | (2006.01) |
| *C08F 20/26* | (2006.01) |
| *A61K 31/785* | (2006.01) |
| *A61K 49/04* | (2006.01) |
| *C08L 33/14* | (2006.01) |
| *A61B 17/00* | (2006.01) |
| *A61B 90/00* | (2016.01) |

(52) U.S. Cl.
CPC .. *A61B 17/12181* (2013.01); *A61B 17/12186* (2013.01); *A61K 31/785* (2013.01); *A61K 49/0438* (2013.01); *A61K 49/0442* (2013.01); *C08F 20/26* (2013.01); *A61B 2017/00938* (2013.01); *A61B 2017/00942* (2013.01); *A61B 2090/3933* (2016.02); *A61B 2090/3966* (2016.02); *C08L 33/14* (2013.01)

(58) Field of Classification Search
CPC ........ A61B 17/12181; A61B 17/12186; A61K 31/785
See application file for complete search history.

(56) References Cited

U.S. PATENT DOCUMENTS

| 3,852,341 A | 12/1974 | Bjork et al. |
| 4,406,878 A | 9/1983 | Boer et al. |
| 5,580,568 A | 12/1996 | Greff et al. |
| 5,667,767 A | 9/1997 | Greff et al. |
| 5,695,480 A | 12/1997 | Evans et al. |
| 5,702,361 A | 12/1997 | Evans et al. |
| 5,755,658 A | 5/1998 | Wallace et al. |
| 5,823,198 A | 10/1998 | Jones et al. |
| 5,830,178 A | 11/1998 | Jones et al. |
| 5,851,508 A | 12/1998 | Greff et al. |
| 5,894,022 A | 4/1999 | Ji et al. |
| 6,004,573 A | 12/1999 | Rathi et al. |
| 6,015,541 A | 1/2000 | Greff et al. |
| 6,017,977 A | 1/2000 | Evans et al. |
| 6,037,366 A | 3/2000 | Krall et al. |
| 6,040,408 A | 3/2000 | Koole |
| 6,051,607 A | 4/2000 | Greff et al. |
| 6,146,373 A | 11/2000 | Cragg et al. |
| 6,281,263 B1 | 8/2001 | Evans et al. |
| 6,303,100 B1 | 10/2001 | Ricci et al. |
| 6,333,020 B1 | 12/2001 | Wallace et al. |
| 6,335,384 B1 | 1/2002 | Evans et al. |
| 6,342,202 B1 | 1/2002 | Evans et al. |
| 6,394,945 B1 | 5/2002 | Chan et al. |
| 6,454,738 B1 | 9/2002 | Tran et al. |
| 6,475,477 B1 | 11/2002 | Kohn et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,558,367 B1 | 5/2003 | Cragg et al. |
| 6,562,362 B1 | 5/2003 | Bae et al. |
| 6,565,551 B1 | 5/2003 | Jones et al. |
| 6,569,190 B2 | 5/2003 | Whalen et al. |
| 6,599,448 B1 | 7/2003 | Ehrhard et al. |
| 6,602,269 B2 | 8/2003 | Wallace et al. |
| 6,610,046 B1 | 8/2003 | Usami et al. |
| 6,616,591 B1 | 9/2003 | Teoh et al. |
| 6,623,450 B1 | 9/2003 | Dutta et al. |
| 6,645,167 B1 | 11/2003 | Whalen, II et al. |
| 6,699,222 B1 | 3/2004 | Jones et al. |

(Continued)

FOREIGN PATENT DOCUMENTS

| CA | 2551373 C | 6/2014 |
| CN | 101513542 B | 8/2012 |

(Continued)

OTHER PUBLICATIONS

Machine translation of JP1993-253283A. 2018, pp. 1-7 (Year: 2018).*
Kocer, N. et al. "Preliminary experience with precipitating hydrophobic injectable liquid in brain arteriovenous malformations" Diagn Interv Radiol Jan. 19, 2016; 22:184-189 (Year: 2016).*
Argawal et al., Chitosan-based systems for molecular imaging. Advanced Drug Delivery Reviews, 62:42-48 (2010).
Dudeck O, Jordan O, Hoffmann KT, et al. Embolization of experimental wide-necked aneurysms with iodine-containing polyvinyl alcohol solubilized in a low-angiotoxicity solvent. AJNR Am J Neuroradiol. 2006;27(9):1849-1855.
Dudeck O, Jordan O, Hoffmann KT, et al. Organic solvents as vehicles for precipitating liquid embolics: a comparative angiotoxicity study with superselective injections of swine rete mirabile. AJNR Am J Neuroradiol. 2006;27(9):1900-1906.

(Continued)

*Primary Examiner* — Andrew S Rosenthal
(74) *Attorney, Agent, or Firm* — K&L Gates LLP; Brian J. Novak; Georgia N. Kefallinos

(57) ABSTRACT

Described herein are compositions comprising, a polymer; a non-physiological solution; and a visualization agent; wherein the polymer is soluble in the non-physiological solution and insoluble at physiological conditions. Methods of preparing the compositions are disclosed as well as methods of using these compositions to treat vascular conditions.

23 Claims, 5 Drawing Sheets

(56) References Cited

U.S. PATENT DOCUMENTS

| | | |
|---|---|---|
| 6,756,031 B2 | 6/2004 | Evans et al. |
| 6,759,028 B2 | 7/2004 | Wallace et al. |
| 6,962,689 B2 | 11/2005 | Whalen et al. |
| 6,964,657 B2 | 11/2005 | Cragg et al. |
| 6,979,464 B2 | 12/2005 | Gutowska |
| 7,018,365 B2 | 3/2006 | Strauss et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,776,063 B2 | 8/2010 | Sawhney et al. |
| 7,790,141 B2 | 9/2010 | Pathak et al. |
| 7,838,699 B2 | 11/2010 | Schwarz et al. |
| 7,976,527 B2 | 7/2011 | Cragg et al. |
| 8,066,667 B2 | 11/2011 | Hayman et al. |
| 8,235,941 B2 | 8/2012 | Hayman et al. |
| 8,454,649 B2 | 6/2013 | Cragg et al. |
| 8,486,046 B2 | 7/2013 | Hayman et al. |
| 8,492,329 B2 | 7/2013 | Shemesh et al. |
| 8,685,367 B2 | 4/2014 | Brandom et al. |
| 9,351,993 B2 | 5/2016 | Cruise et al. |
| 9,434,800 B2 | 9/2016 | Chevalier et al. |
| 9,655,989 B2 | 5/2017 | Cruise et al. |
| 2001/0022962 A1 | 9/2001 | Greff et al. |
| 2001/0024637 A1 | 9/2001 | Evans et al. |
| 2001/0033832 A1 | 10/2001 | Wallace et al. |
| 2001/0036451 A1 | 11/2001 | Goupil et al. |
| 2001/0046518 A1 | 11/2001 | Sawhney |
| 2002/0026234 A1 | 2/2002 | Li et al. |
| 2002/0042378 A1 | 4/2002 | Reich et al. |
| 2003/0021762 A1 | 1/2003 | Luthra et al. |
| 2003/0040733 A1 | 2/2003 | Cragg et al. |
| 2003/0100942 A1 | 5/2003 | Ken et al. |
| 2003/0211083 A1 | 11/2003 | Vogel et al. |
| 2003/0232198 A1 | 12/2003 | Lamberti et al. |
| 2004/0024098 A1 | 2/2004 | Mather et al. |
| 2004/0091425 A1 | 5/2004 | Boschetti |
| 2004/0091543 A1 | 5/2004 | Bell et al. |
| 2004/0157082 A1 | 8/2004 | Ritter et al. |
| 2004/0158282 A1 | 8/2004 | Jones et al. |
| 2004/0161547 A1 | 8/2004 | Carlson et al. |
| 2004/0209998 A1 | 10/2004 | De Vries |
| 2004/0224864 A1 | 11/2004 | Patterson et al. |
| 2004/0228797 A1 | 11/2004 | Bein et al. |
| 2004/0241158 A1 | 12/2004 | McBride et al. |
| 2005/0003010 A1 | 1/2005 | Cohen et al. |
| 2005/0008610 A1 | 1/2005 | Schwarz et al. |
| 2005/0106119 A1 | 5/2005 | Brandom et al. |
| 2005/0123596 A1 | 6/2005 | Kohane et al. |
| 2005/0143484 A1 | 6/2005 | Fang et al. |
| 2005/0175709 A1 | 8/2005 | Baty et al. |
| 2005/0196449 A1 | 9/2005 | DiCarlo et al. |
| 2005/0226935 A1 | 10/2005 | Kamath et al. |
| 2005/0244504 A1 | 11/2005 | Little et al. |
| 2005/0265923 A1 | 12/2005 | Toner et al. |
| 2006/0008499 A1 | 1/2006 | Hudak |
| 2006/0067883 A1 | 3/2006 | Krom et al. |
| 2006/0069168 A1 | 3/2006 | Tabata et al. |
| 2006/0088476 A1 | 4/2006 | Harder et al. |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237741 A1 | 10/2007 | Figuly et al. |
| 2007/0248567 A1 | 10/2007 | Pathak et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0214695 A1 | 9/2008 | Pathak et al. |
| 2008/0226741 A1 | 9/2008 | Richard |
| 2008/0243129 A1 | 10/2008 | Steffen et al. |
| 2008/0269874 A1 | 10/2008 | Wang et al. |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0093550 A1 | 4/2009 | Rolfes et al. |
| 2009/0117033 A1 | 5/2009 | O'Gara |
| 2009/0117070 A1 | 5/2009 | Daniloff et al. |
| 2009/0181068 A1 | 7/2009 | Dunn |
| 2009/0186061 A1 | 7/2009 | Griguol et al. |
| 2009/0215923 A1 | 8/2009 | Carnahan et al. |
| 2009/0221731 A1 | 9/2009 | Vetrecin et al. |
| 2009/0259302 A1 | 10/2009 | Trollsas et al. |
| 2009/0297612 A1 | 12/2009 | Koole et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0049165 A1 | 2/2010 | Sutherland et al. |
| 2010/0080788 A1 | 4/2010 | Barnett et al. |
| 2010/0086678 A1 | 4/2010 | Arthur et al. |
| 2010/0158802 A1 | 6/2010 | Hansen et al. |
| 2010/0247663 A1 | 9/2010 | Day et al. |
| 2010/0256777 A1 | 10/2010 | Datta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0071495 A1 | 3/2011 | Tekulve |
| 2011/0091549 A1 | 4/2011 | Blaskovich et al. |
| 2011/0105889 A1 | 5/2011 | Tsukada et al. |
| 2011/0182998 A1 | 7/2011 | Reb et al. |
| 2011/0190813 A1 | 8/2011 | Brownlee et al. |
| 2011/0202016 A1 | 8/2011 | Zugates et al. |
| 2012/0041481 A1 | 2/2012 | Daniloff et al. |
| 2012/0059394 A1 | 3/2012 | Brenner et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Baiting et al. |
| 2012/0238644 A1 | 9/2012 | Gong et al. |
| 2012/0244198 A1 | 9/2012 | Malmsjo et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0184660 A1 | 7/2013 | Swiss et al. |
| 2013/0225778 A1 | 8/2013 | Goodrich et al. |
| 2014/0039459 A1 | 2/2014 | Folk et al. |
| 2014/0056806 A1 | 2/2014 | Vemengo et al. |
| 2014/0107251 A1 | 4/2014 | Cruise et al. |
| 2014/0171907 A1 | 6/2014 | Golzarian et al. |
| 2014/0274945 A1 | 9/2014 | Blaskovich et al. |
| 2014/0277057 A1 | 9/2014 | Ortega et al. |
| 2015/0290344 A1 | 10/2015 | Alexis et al. |
| 2016/0243157 A1 | 8/2016 | Cruise et al. |
| 2016/0279282 A1* | 9/2016 | Cruise .................... A61L 24/06 |
| 2017/0216484 A1 | 8/2017 | Cruise et al. |
| 2017/0274101 A1 | 9/2017 | Hainfeld |
| 2018/0055516 A1 | 3/2018 | Baldwin et al. |
| 2018/0200288 A1 | 7/2018 | Cruise et al. |
| 2019/0105425 A1 | 4/2019 | Cruise et al. |
| 2019/0134078 A1 | 5/2019 | Cruise et al. |
| 2019/0192726 A1 | 6/2019 | Cruise et al. |

FOREIGN PATENT DOCUMENTS

| | | | |
|---|---|---|---|
| CN | 102107025 B | 5/2014 | |
| EP | 1601392 A1 * | 12/2005 | ......... A61K 49/0002 |
| EP | 1599258 B1 | 8/2008 | |
| EP | 1601392 B1 | 4/2009 | |
| EP | 1558299 B1 | 12/2012 | |
| JP | 05-057014 | 3/1993 | |
| JP | 1993253283 A * | 10/1993 | |
| JP | 1993253283 A | 10/1993 | |

(56) References Cited

FOREIGN PATENT DOCUMENTS

| | | |
|---|---|---|
| JP | 11-166018 | 6/1999 |
| WO | 1996/005872 | 2/1996 |
| WO | 2004/073843 A1 | 9/2004 |
| WO | 2005/013810 A2 | 2/2005 |
| WO | 2005/030268 A1 | 4/2005 |
| WO | 2006/095745 A1 | 9/2006 |
| WO | 2008/118662 A2 | 10/2008 |
| WO | 2011/110589 A1 | 9/2011 |
| WO | 2012/025023 A1 | 3/2012 |
| WO | 2012/088896 A1 | 7/2012 |
| WO | 2012/171478 A1 | 12/2012 |
| WO | 2013/188681 A1 | 12/2013 |
| WO | 2014/062696 A1 | 4/2014 |
| WO | 2014/152488 A2 | 9/2014 |
| WO | 2019/074965 A1 | 4/2019 |

OTHER PUBLICATIONS

He et al., Material properties and cytocompatibility of injectable MMP degradable poly(lactide ethylene oxide fumarate) hydrogel as a carrier for marrow stromal cells. Biomacromolecules, vol. 8, pp. 780-792 (2007).

Levasque et al., Synthesis of enzyme-degradable, peptide-cross-linked dextran hydrogels. Bionconjugate Chemistry, vol. 18, pp. 874-885 (2007).

Moss et al., Solid-Phase synthesis and kinetic characterization of fluorogenic enzyme-degradable hydrogel cross-linkers. Biomacromolecules, vol. 7, pp. 1011-1016 (2006).

Onyx Liquid Embolic System Onyx HD-500, Instructions for Use, ev3 Endovascular, Inc., Nov. 2007.

Supplementary European Search Report dated Sep. 26, 2016 for European Patent Application No. 13846860.8 filed on Oct. 15, 2013.

Takao H, Murayama Y, Yuki I, et al. Endovascular treatment of experimental aneurysms using a combination of thermoreversible gelation polymer and protection devices: feasibility study. Neurosurgery. 2009;65(3):601-609.

Jayakrishnan et al., Synthesis and polymerization of some iodine-containing monomers for biomedical applications. Journal of Applied Polymer Science, vol. 44, pp. 743-748 (1992).

International Search Report and Written Opinion, dated Dec. 31, 2018, for International Application No. PCT/US2018/055074.

Wikipedia, "Isotopes of Iodine" Version: Jun. 15, 2017, Retrieved: Nov. 26, 2018 (https://en.wikipedia.org/w/index.php?title=isotopes_of_iodine&oldid=785724472), p. 2, para 7.

Arslan et al., Use of 4-vinylpyridine and 2-hydroxyethylmethacrylate monomer mixture grafted poly(ethylene terephthalate) fibers for removal of congo red from aqueous solution. E-Polymers, vol. 8, Issue 1, 016, pp. 1-15 (2008).

Shin et al., Inverse opal pH sensors with various protic monomers copolymerized with polyhydroxyethylmethacrylate hyrdrogel. Analytica Chimica Acta, 752:87-93 (2012).

Yi et al., Ionic strength/temperature-induced gelation of aqueous poly(N-isopropylacrylamide-co-vinylimidazole) solution. Macromol. Symp. 207, pp. 131-137 (2004).

Kocer et al., Preliminary experience with precipitating hydrophobic injectable liquid in brain arteriovenous malformations. Diagn Interv Radiol, 22:184-189 (2016).

International Search Report and Written Opinion, dated Jan. 2, 2014, for International Application No. PCT/US2013/065078.

International Search Report for International Application No. PCT/US2013/045692 filed on Jun. 13, 2013.

U.S. Appl. No. 16/750,635, filed Jan. 23, 2020.

U.S. Appl. No. 16/806,936, filed Mar. 2, 2020.

\* cited by examiner

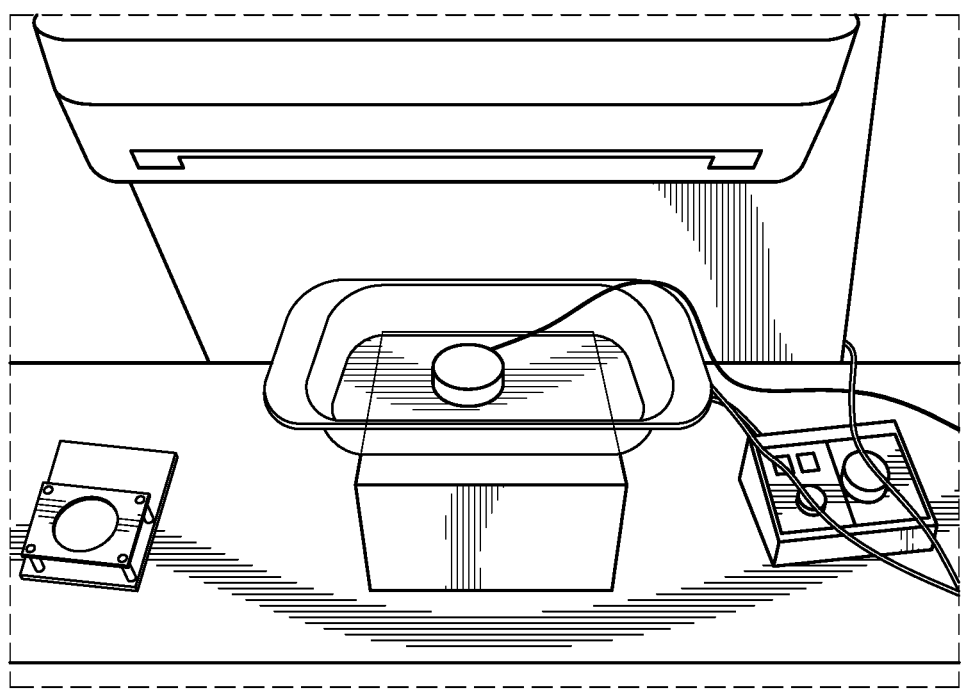
FIG 1
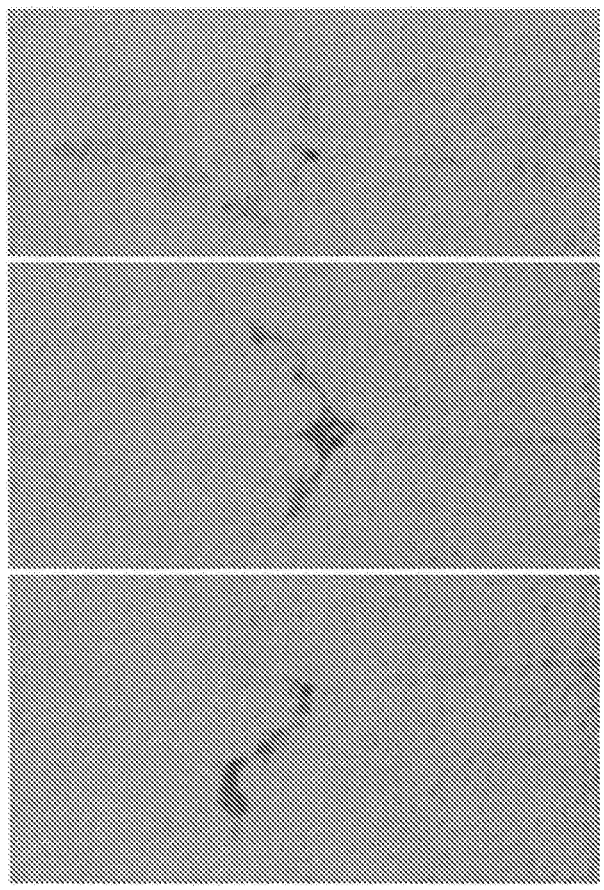
FIG. 2A
FIG. 2B
FIG. 2C

EMBOLIC COMPOSITIONS

CROSS REFERENCE TO RELATED APPLICATIONS

This application is a continuation of U.S. patent application Ser. No. 15/687,263, filed Aug. 25, 2017, which claims the benefit of U.S. provisional patent application No. 62/380,317, filed Aug. 26, 2016, the entire disclosure of each of which is incorporated herein by reference.

FIELD

The present invention relates generally to vascular treatment compositions and methods of using these compositions to treat vascular conditions. The compositions can comprise a polymer(s) that transitions from a liquid to a solid upon being subjected to physiological conditions.

BACKGROUND

Embolization is widely used to treat vascular malformations, such as aneurysms, arteriovenous malformations, fistulas, and tumors. These malformations can be treated with a variety of different products, including metallic coils, polymer-metal hybrid coils, microparticles, and foams. However, there remains a need for products that can minimize risks associated with embolization.

SUMMARY

Polymeric compositions are described which comprise: a biocompatible polymer, a visualization agent, and a non-physiological solution; wherein the biocompatible polymer is soluble in the non-physiological solution and insoluble at physiological conditions. In some embodiments, the visualization agent is integrated, e.g., chemically integrated, into the biocompatible polymer. In other embodiments, the visualization agent is associated with the biocompatible polymer. In other embodiments, the visualization agent may not be integrated into the biocompatible polymer. In some embodiments, the polymer need not be biocompatible.

In some embodiments, the solubility change from non-physiological to physiological conditions can be instantaneous. The solubilized polymer can become an insoluble mass instantaneously. Instantaneous can be in less than about 0.1 s, less than about 0.5 s, less than about 1 s, or less than about 5 s.

Methods of using polymeric compositions are also described. In one embodiment, methods are described comprising injecting through a delivery device into a physiological environment a liquid embolic composition. The liquid embolic composition can comprise a biocompatible polymer, a visualization agent, and a non-physiological solution, wherein the biocompatible polymer precipitates when it reaches the physiological conditions.

In one embodiment, methods are described comprising injecting through a delivery device into a vessel with physiological environment a liquid embolic composition. The liquid embolic composition can comprise a biocompatible polymer, a visualization agent, and a water-miscible organic solvent, wherein the biocompatible polymer precipitates when it reaches the physiological conditions and treats the vascular disorder.

In another embodiment, methods are described comprising providing a liquid embolic composition. The liquid embolic composition can comprise a biocompatible polymer, a visualization agent, and a non-physiological pH aqueous solution. The biocompatible polymer can be soluble in the non-physiological pH aqueous solution and insoluble at physiological conditions. In one embodiment, a delivery device can be inserted into a vessel and guided to an area in need of treatment wherein the area has physiological conditions. The liquid embolic polymer composition can then be injected through the delivery device into the vessel at the area in need of treatment thereby immediately precipitating the polymer and forming a solid polymeric mass and treating the vascular condition.

In another embodiment, methods are described comprising providing a liquid embolic composition comprising a biocompatible polymer, a visualization agent, and a water-miscible organic solvent. The biocompatible polymer can be soluble in the organic solvent and insoluble at physiological conditions. In one embodiment, a delivery device can be inserted into a vessel and guided to an area in need of treatment. The liquid embolic polymer composition can then be injected through the delivery device into the vessel at the area in need of treatment thereby immediately precipitating the polymer and forming a solid polymeric mass and treating the vascular condition.

Additional features and advantages are described herein, and will be apparent from the following Detailed Description and figures.

BRIEF DESCRIPTION OF THE DRAWINGS

FIG. 1 illustrates an experimental apparatus for Example 1.

FIGS. 2A-2C illustrate a comparison of radiopacity of embolics with different radiopaque materials. FIG. 2A illustrates radiopacity of PHIL 20% w/w. FIG. 2B illustrates radiopacity of PHIL 20% w/w+iohexol 30% w/w. FIG. 2C illustrates radiopacity of PHIL 20% w/w+triiodophenol 30% w/w.

DETAILED DESCRIPTION

Figure 3:
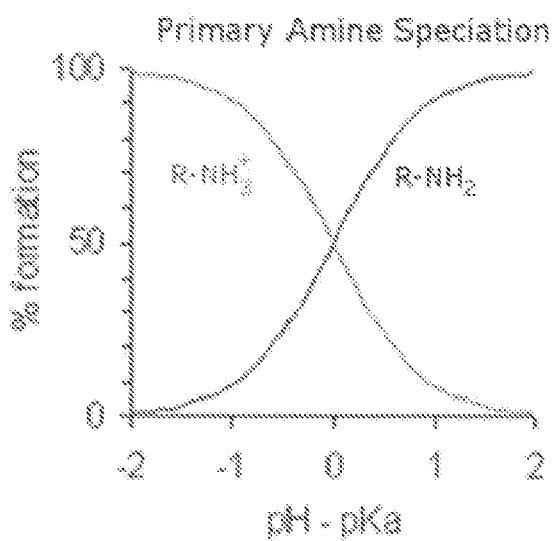
FIG. 3 illustrates pKa curves for primary amines.

Described herein generally are polymeric compositions. These compositions can include biocompatible polymers and visualization agents. In some embodiments, the biocompatible polymers can be soluble in selected solvent systems and insoluble at physiological conditions or in a physiological solution/fluid in a selected solvent. In other embodiments, the visualization agents can be an opacification agent(s) that can permit visualization in vivo. In other embodiments, the solution can include a miscible solvent that can dissolve the polymer. In some embodiments, the miscible solvent can be a water miscible solvent. In other embodiments, the miscible solvent can be a water miscible organic solvent diluted with water. In certain embodiments, the polymeric compositions can include a catheter flush solution. In some embodiments, the catheter flush solution can be a miscible organic solvent and/or a miscible organic solvent diluted in water. In other embodiments, the solution can include a non-physiological pH solvent. The compositions can be introduced through a delivery device in a liquid state and transition to a solid state once in contact with a physiological fluid.

When a polymer is soluble in solution, it can be easy to deploy through a delivery device, e.g. microcatheter, to a delivery site and/or treatment site. However, once precipitated out of solution, a polymer can be much more difficult to deploy. For example, once precipitated, a polymer can in some instances be more difficult to deploy through a delivery device. As such, the compositions and methods described herein can provide polymer treatment solutions to sites that would otherwise not be easily administered to without being soluble prior to exiting a delivery device.

The compositions can comprise a solution at a non-physiological condition (e.g. non-physiological pH). The solution can include a polymer soluble in the solution but insoluble at physiological conditions. In some embodiments, the solution can include a polymer soluble in a non-physiological pH aqueous solution but insoluble at physiological conditions. In another embodiment, the polymer can be soluble in a water-miscible organic solvent but insoluble at physiological conditions (e.g. water).

Physiological fluids can include, but are not limited to, blood, urine, saliva, mucous, vaginal fluid, seminal fluid, cerebral spinal fluid, sweat, plasma, bile, stomach acid, intestinal fluids, and the like.

A function of the biocompatible polymer, e.g. liquid embolic polymer, can be to precipitate when coming into contact with blood or other physiological fluid(s). If the pH of the physiological fluid is the solubility trigger, the physiological pH can be a pH of about 7.0, about 7.1, about 7.2, about 7.3, about 7.4, about 7.5, about 7.6, about 7.7 or about 7.8, between about 7.0 and about 7.8, between about 7.1 and about 7.7, between about 7.2 and about 7.6, or any value in a range bound by or between any of these values. The non-physiological pH can be a pH between about 1.0 and about 6.9, or about 2.0 and about 6.0, about 7.9 and about 12.0, about 8.5 and about 10.0. Alternatively, if the solubility trigger is solubility in a water miscible organic solvent and insolubility at physiological conditions, any physiological environment can initiate the precipitation.

Precipitation of the polymer at physiological conditions can be used to occlude a biological structure. Control of the liquid embolic polymer's solubility can be achieved by selection of the composition of the polymer. The polymer can be prepared with monomers having ionizable moieties. In some embodiments, the polymers can be a reaction product of two different monomers, three different monomers, four different monomers, five different monomers, or more. In the case of a pH sensitive solubility trigger, a hydrophobic polymer can be constructed with a minimum amount of ionizable moieties to render the polymer soluble in non-physiological pH solutions. The ratio of monomers with ionizable moieties and other monomers can be dependent on the structure of the monomers and can be determined experimentally.

Monomers used to form the polymers, or otherwise termed embolic polymer or embolic, are described. Embolic materials and embolic formulations including these monomers and polymers including these monomers are also described. Further, methods of making embolic monomers and embolic materials, and methods of using the monomers and embolic materials are described. The embolics described can have increased radiopacity and/or enhanced physical properties when compared to conventional embolic materials.

Liquid embolic devices can be formed of organic soluble polymers. These organic soluble polymers can precipitate upon solvent exchange with water or other solvent, thus acting as an embolic agent when injected intra-arterially or venously.

In some embodiments, embolic polymers can include hydroxyethylmethacrylate (HEMA), lactide, glycolide, polyvinyl pyridine (PVP), alkylalkylacrylate, alkylacrylate, acrylate, styrene, polyvinyl alcohol (PVA), acrylamide, ethylene glycol, combinations thereof, co-polymers thereof, and the like.

In some embodiments, polymers and/or monomers described can include a visualization agent bonded to it. In one embodiment, a visualization agent bonded to the polymer can be triiodophenol-lactide-glycolide (TIP).

In other embodiments, the visualization agent can be a water soluble molecule, which can include, but is not limited to, Iohexol and diatrizoic acid.

In certain embodiments, the visualization agent is a water insoluble molecule, which can include, but is not limited to, triiodophenol or TIP.

In some embodiments, embolic polymers can include hydroxyethylmethacrylate (HEMA), triiodophenol-lactide-glycolide (TIP), polyvinyl pyridine (PVP), PVP-co-polybutylmethacrylate, and PVP-co-styrene, PVP-co-polyvinyl alcohol (PVA) or PVA-co-polyacrylamide.

In one embodiment, an embolic polymer can include about 60% w/w HEMA and about 40% w/w TIP. In another embodiment, an embolic polymer can include about 15% w/w HEMA and about 85% w/w TIP.

In some embodiments, a liquid embolic system includes a polymer dissolved in a solvent. The solvent used to dissolve the monomers can be any solvent that dissolves the desired monomers/polymers. Solvents can include water, methanol, acetonitrile, dimethyl formamide, dimethyl sulfoxide, a co-solvent thereof, or a combination thereof. In one embodiment, a liquid embolic system including a polymer dissolved in a co-solvent of water and dimethyl sulfoxide (DMSO) can precipitate when contacted with water or blood.

Embolic polymers described herein can be pH sensitive and can be formed at least partially of polymers and/or monomers that are water soluble at one pH and insoluble when the pH is altered. Such materials may be beneficial because they may not need organic solvents in order to function. Providing an embolic device that does not require an organic solvent to deploy may be beneficial as many organic solvents can be toxic and/or not physiologically acceptable.

However, finding pH sensitive liquid embolic devices can be challenging because primary amine containing monomers for acid soluble polymers can have drawbacks. In one embodiment, a primary amine is included, such as but not limited to, aminoethyl methacrylate or aminopropylmethacrylamide, which has a pKa of about 10. As a solution pH falls below 10, such amine containing polymers can become protonated; the lower the pH the more they become protonated inducing greater water solubility to the polymer.

Thus, although primary amine containing embolic polymers can have solubility at high pH, the pKa is much greater than physiological pH. The relationship of the amount of positive charged species and distance from the pKa is logarithmic on the ratio of the species present. This relationship is shown mathematically by Equation 1.

$$\text{pH} = pKa + \log\frac{[A-]}{[HA]} \qquad \text{Equation 1}$$

FIG. 3 is a plot of this relationship for amine species. In this case at a pH of 9, a primary amine would be 90% positively charged, and at a pH of 8, 99% positively charged. Thus, a diminishing return may be experienced for decreasing the solution pH as one gets further away from the pKa. Consequently, when using primary amines to solubilize a polymer, an extremely low solution pH (e.g., pH 3) may be required.

In one embodiment, an amine is included that requires a less acidic solution and/or has a lower pKa. A subset of amine monomers that have these criterions may be aromatic amines and may be included in the herein described polymers. Aromatic amines have pKa's ranging from about 5.6 to about 6.0, inducing a greater solubility shift compared to primary amines.

In one embodiment, an aromatic amine can be 1-vinylimidazole having a pKa of about 6.0. This aromatic amine would be about 90% positively charged at a pH of 5, and only about 10% positively charged at a pH of 7.

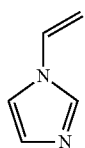

1-Vinylimidazole

In comparison, a primary amine such as aminoethyl methacrylate (AEMA) can be 99.999% positively charged at a pH of 5 and 99.9% positively charged at a pH of 7. Some embodiments may include this amine.

In another embodiment, an aromatic amine can be 4-vinylpyridine.

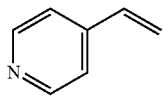

4-VinylPyridine

In some embodiments, an aromatic amine monomer(s) can be combined with other hydrophilic or hydrophobic monomers to create a polymer which would have desired precipitation characteristics. Therein, the aromatic amine would induce the pH sensitivity, and a hydrophobic monomer would aid in the water precipitation and/or a hydrophilic monomer would aid in solubility.

Embolic compositions, in some embodiments, can include both hydrophilic and hydrophobic monomers incorporated into the polymer chain. For example, vinyl alcohol and hydroxyethylmethacrylate are hydrophilic components which can be included in the herein described embolic polymers. Because of the dual hydrophilic/hydrophobic nature of the polymer backbone, a certain amount of water can be incorporated into the organic solvent without causing precipitation.

In some embodiments, a co-solvent system can be used to dissolve embolic polymers more efficiently. In one embodiment, the co-solvent system is a water-DMSO co-solvent system. In other embodiments, water:DMSO mixture ratios may range from 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1.

Figure 5:
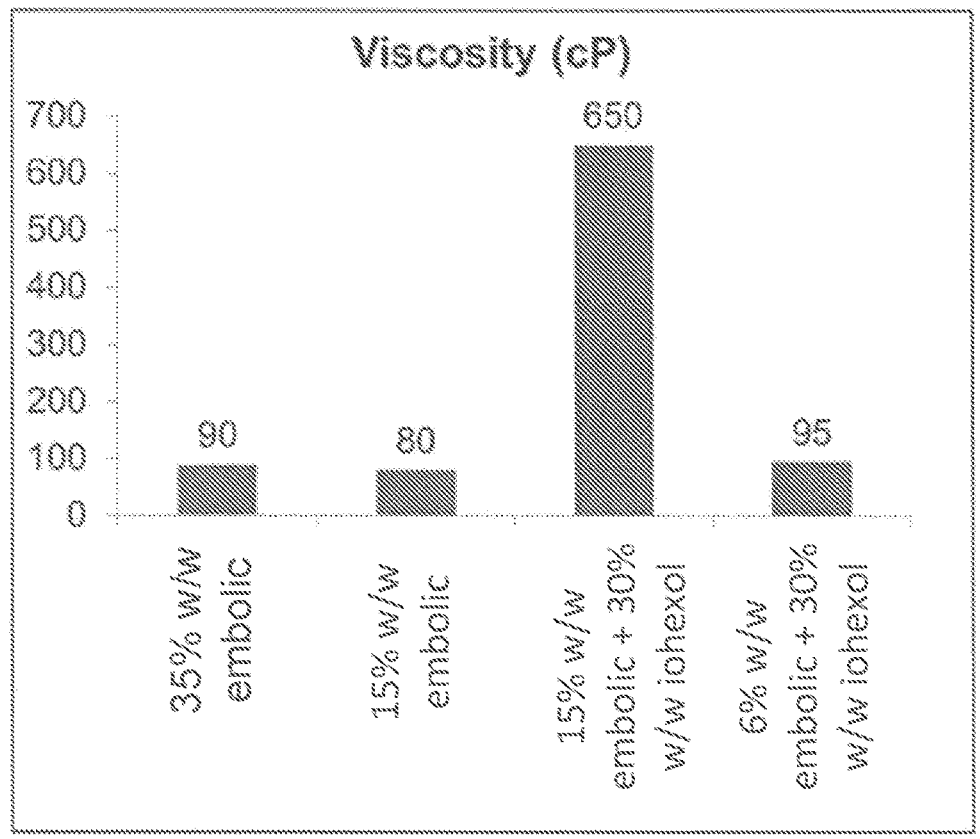
FIG. 5 illustrates a comparison of different embolic compositions with and without a radiopaque material.

In embodiments where the embolic polymer includes increased amounts of HEMA, the embolic polymer may impart greater cohesiveness at the cost of lower radiopacity and/or higher viscosity. In order to offset the potentially lower radiopacity, a contrast agent/radiopaque material can be added. However, in some embodiments, addition of a radiopaque material can increase the viscosity; this is illustrated in FIG. 5.

In some embodiments, to counteract an increased viscosity, a reduced amount of embolic polymer can be used to allow for syringe injection.

Figure 6:
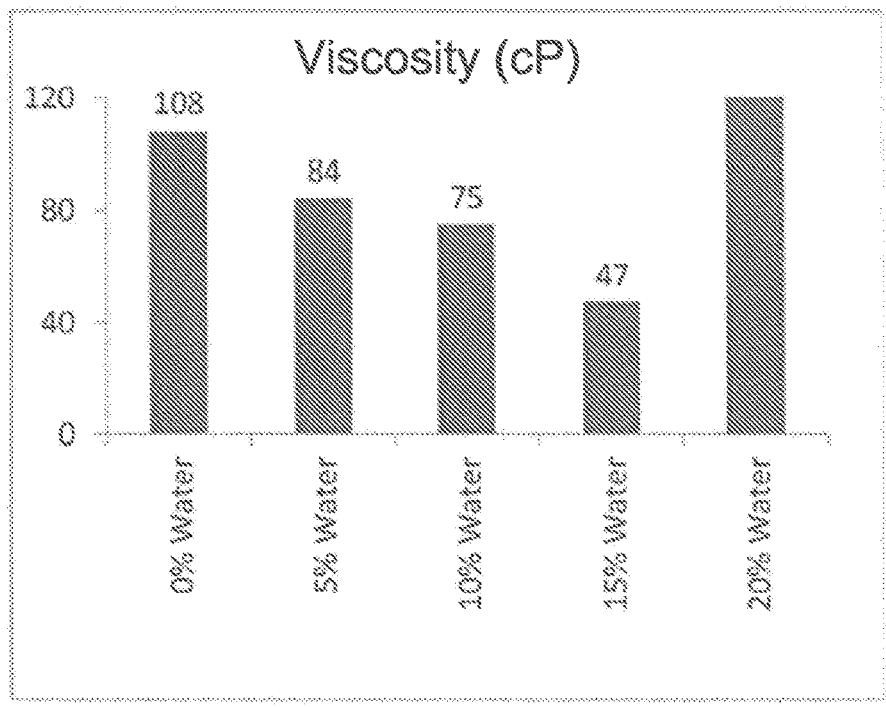
FIG. 6 illustrates water addition impact on the viscosity of a 9% w/w embolic polymer containing 30% w/w Iohexol. Twenty percent water addition can cause the solution to gel and the viscosity was not measured. Therefore, a high bar was added to the figure for reference.

In other embodiments, viscosity of an embolic polymer can be reduced by addition of water to the solvent. In one embodiment, an embolic composition including about 6% w/w polymer and 30% Iohexol has similar viscosity to a 35% w/w embolic polymer concentration, the precipitation performance of the material may be poor. In one embodiment, the viscosity of this embolic polymer can be reduced by the addition of water (FIG. 6).

In some embodiments, increasing the water content in the solvent from 0 to 15% w/w can decrease viscosity. In one embodiment, when the water concentration exceeds about 20% w/w, the solution may begin to gel and not flow.

When water can be added to the solvent, a co-solvent can expose a patient to less potentially harmful solvent. In one embodiment, when DMSO is used as a solvent, a water-DMSO co-solvent system exposes a patient to less DMSO. Reducing the total DMSO burden on a patient may reduce vasospasm and/or other toxic side effects from DMSO.

In some embodiments, water addition to the solvent can modulate the viscosity of the embolic by the amount of water incorporated into the formulation. Further, in other embodiments, water incorporation can change how the polymer precipitates. For example, in one embodiment, an embolic in a solvent with no water would have a reduced viscosity before precipitating (see FIG. 7), possibly allowing the liquid embolic to flow more easily. In contrast, an embolic formulation with 15% w/w water would not have a reduction in viscosity before precipitation and may lead to more control over the embolic resulting from a reduced flow.

Embolic systems can include up to about 1% w/w, up to about 2% w/w, up to about 3% w/w, up to about 4% w/w, up to about 5% w/w, up to about 6% w/w, up to about 7% w/w, up to about 8% w/w, up to about 9% w/w, up to about 10% w/w, up to about 15% w/w, up to about 20% w/w, up to about 25% w/w, up to about 30% w/w, up to about 35% w/w, up to about 40% w/w, or up to about 50% w/w water before the embolic polymer precipitates. In some embodiments, the amount of water that an embolic solvent can contain without the embolic polymer precipitating can be dependent on the amount of HEMA; the more HEMA, the more water can be included in the solvent.

In one embodiment, the embolic system can comprise about 85% w/w/l TIP, about 15% w/w HEMA, and about 20% w/w DMSO with up to about 5% w/w water. In another embodiment, the embolic system can comprise about 40% w/w/TIP, about 60% w/w HEMA, and about 8% w/w DMSO with up to about 20% w/w water, or about 9% w/w DMSO with up to about 15% w/w water, or about 10% w/w DMSO with up to about 15% w/w water. In yet another embodiment, the embolic system can comprise about 50% w/w/TIP, about 50% w/w HEMA, and about 7% w/w DMSO with up to about 7.0% w/w water, or about 7.5% w/w DMSO with up to about 7.5% w/w water, or about 8% w/w DMSO with up to about 7.5% w/w water, or about 9% w/w DMSO with up to about 10% w/w water.

In one embodiment, when the embolic is present at 35% w/w, the solvent can contain about 5% w/w water. In other embodiments, when the embolic includes a higher HEMA concentration, the solvent can contain more than about 15% w/w water before precipitation.

A co-solvent system can also be used with an embolic system such as ONYX® (Covidien). ONYX is a polyethylene vinyl alcohol based, non-adhesive liquid embolic agent used for the pre-surgical embolization of brain arteriovenous malformations (bAVM).

A co-solvent system can also be used with embolic systems that utilize particulates for radiopacity. These particulates can include tantalum, tungsten, barium sulfate, etc rather than an incorporated TIP or contrast agent.

In some embodiments, viscosity of the herein described embolic polymers can be reduced when compared to a conventional embolic polymer. In other embodiments, viscosity can be reduced, and the embolic polymer may be increased. Such a combination may lead to a better precipitating solution.

In some embodiments, the embolic can be a precipitating hydrophobic injectable liquid (PHIL). A PHIL material can include a polymer molecule comprising triiodophenol-lactide-co-glycolide acrylate and HEMA. Triiodophenol is an iodine component that can be chemically bonded to the co-polymer to provide fluoroscopic visualization.

As described herein, the embolic PHIL polymer can be dissolved in DMSO or another appropriate solvent to formulate a liquid version wherein the polymer is dissolved. Generally, a higher polymer concentration in DMSO, a higher viscosity and a higher material radiopacity. In one embodiment, a PHIL with 25% w/w polymer and 75% w/w DMSO offers just adequate radiopacity. If the polymer concentration is lowered, radiopacity is lowered, thereby creating unsafe conditions and a possibly unusable embolic polymer solution. However, a formulation that if viscosity can be reduced, the embolic polymer can travel more distal for delivery which may be desirable.

In some embodiments, monomers used to form the herein described embolic polymers can include triiodophenol-lactide glycolide acrylate. Production of this monomer can include a step of reacting triiodophenol with lactide glycolide and acryloyl chloride. Generally, one molecule of triiodophenol can be reacted with two molecules of lactide, one molecule of glycolide, and one molecule of acryloyl chloride. A resulting monomer can have a molecular weight of 930 g/mol and have three atoms of iodine. Since iodine has a molecular weight of 126.9 g/mol, 380.7 g/mol of the monomer is attributed to iodine. Thus, the weight of iodine can account for about 40.7% of a monomer's weight.

In some embodiments, the amount of non-iodine components can be reduced during monomer synthesis. In one embodiment, one molecule of triiodophenol can be reacted with one molecule of lactide (instead of two) and one molecule of glycolide and one molecule of acryloyl chloride. A resulting monomer can have a molecular weight of 786 g/mol with iodine now contributing the same three atoms, which increases the iodine concentration from about 40.7% to about 48% of the monomer's weight.

In some embodiments, the embolics described herein can have a radiopacity that decreases over time. Such an embolic can include a degradable linkage between the iodine-containing group and the main body of the polymer. In one embodiment, this linkage can be a lactide-glycolide linkage between the iodine-containing group and the main body of the polymer. In some embodiments, water may be unable to access the solid, hydrophobic polymer. Thus, functionality of PLGA may be limited in the embolic molecule and reducing its percentage may have an impact on the embolic's properties in some embodiments.

In some embodiments, embolics are provided with an increased radiopacity when compared to conventional embolics. An increased radiopacity can be achieved by including a higher percentage of iodine in the monomer used to form the embolic. In some embodiments, the percent of iodine in a monomer can be greater than about 42% w/w, greater than about 43% w/w, greater than about 44% w/w, greater than about 45% w/w, greater than about 46% w/w, greater than about 47% w/w, greater than about 48% w/w, greater than about 49% w/w, or greater than about 50% w/w.

If a monomer has a higher percent of iodine, it will increase radiopacity for PHIL 25, 30 and 35.

In some embodiments, embolics are provided with a lower viscosity than conventional embolics. This can potentially facilitate making PHIL 20 or PHIL 15 with acceptable radiopacity.

In some embodiments, embolics are provided with an increased cohesivity than conventional embolics. In some embodiments, cohesiveness can be increased by reducing the concentration of triiodophenol, increasing the concentration of hydroxyethylmethacrylate (HEMA), or both.

Some embodiments provide embolic compositions having a viscosity of less than about 16 centistoke, less than about 15 centistoke, less than about 14 centistoke, less than about 13 centistoke, less than about 12 centistoke, less than about 11 centistoke, less than about 10 centistoke, less than about 9 centistoke, less than about 8 centistoke, or less than about 7 centistoke. In one embodiment, an embolic is provided with a viscosity less than about 16 centistoke.

In some embodiments, an embolic with a lower viscosity, e.g., less than about 16 centistoke, may be able to penetrate distally. A reduced viscosity liquid embolic can potentially penetrate further distally during an embolic procedure. This can be attributed to several concepts: 1) a reduced viscosity liquid embolic precipitate can have less cohesion and therefore can be transported downstream further with blood flow during initial precipitation in comparison to a higher viscosity embolic and 2) a reduced viscosity liquid embolic can require less injection force to fill voids/channels in an embolic cast and therefore can penetrate more distally when compared with a more viscous liquid embolic.

Generally, physicians use diluted N-butyl-2-cyanoacrylate (nBCA) in cases where distal penetration is required. The presently described embolics and embolic compositions can provide flow control/arrest without fragmentation. This lack of fragmentation is unlike nBCA where fragmentation is common.

In some embodiments, an embolic can be triiodophenol lactide-glycolide (monomer) bonded with HEMA. In one embodiment, the embolic includes about 85% monomer and about 15% HEMA in the embolic molecule. The higher concentration of the embolic molecule in the solvent, the higher the viscosity and the higher the radiopacity. In some embodiments, the solvent can be DMSO.

In some embodiments, an embolic monomer concentration of about 25% is about the lowest concentration that can achieve acceptable radiopacity. The presently described embolics can achieve acceptable radiopacity with lower concentrations of embolic monomer. In some embodiments, embolic monomers at concentrations of less than about 25%, less than about 20%, less than about 15%, or less than about 10% can achieve acceptable radiopacity.

Radiopacity of embolics described herein can be provided by radiopaque compounds including iodinated compounds, metal particles, barium sulfate, superparamagnetic iron oxide, gadolinium, tantalum, tungsten carbide, molybdenum, rhenium, or a combination thereof.

In one embodiment, an embolic is provided in a solvent and includes barium sulfate.

In another embodiment, an embolic is provided in a solvent and includes superparamagnetic iron oxide.

In another embodiment, an embolic is provided in a solvent and includes gadolinium.

In another embodiment, an embolic is provided in a solvent and includes tungsten carbide.

In another embodiment, an embolic is provided in a solvent and includes molybdenum.

In another embodiment, an embolic is provided in a solvent and includes rhenium.

In one embodiment, an embolic composition is provided including an embolic, dimethyl sulfoxide (DMSO), and a radiopaque material.

Other embodiments provide various components in syringes for delivery. For example, in one embodiment, an embolic composition is provided in a first syringe, DMSO is provided in a second syringe, and a radiopaque mineral can be provided in a third syringe. The embolic composition in the first syringe can include a radiopaque mineral in some embodiments. In other embodiments, the syringes can be provided as kits including a solvent compatible four-way stop cock. In one embodiment, the four-way stop cock can be a DMSO compatible four-way stop cock.

In some embodiments, radiopacity of embolics can be by adding one or more solvent soluble radiopacifying molecules (excipient). In some embodiments, the solvent soluble radiopacifying molecules can be DMSO soluble radiopacifying molecules. The excipient can be one that is also soluble in water. In some embodiments, the excipient can include a radiopacifying atom such as iodine, or bromine, but can also include elements outside of group 17 of the periodic table.

In one embodiment, excipients can be diatrizoic acid based monomers.

In another embodiment, excipients can include iohexol or triiopdophenol.

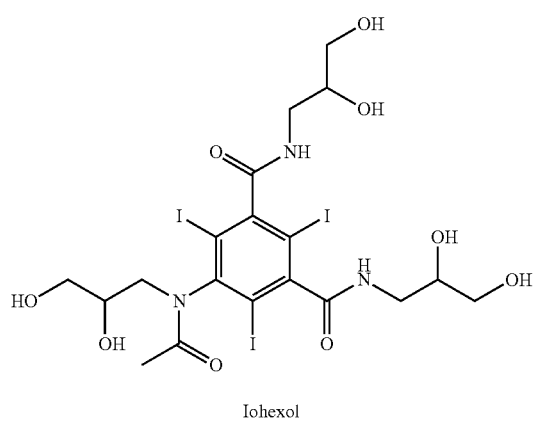

Iohexol

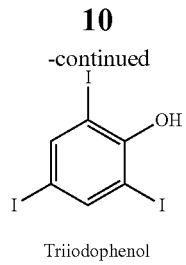

Triiodophenol

Monomers and embolic materials described herein are substantially non-toxic.

Liquid embolic products generally use a solvent to pre-flush a delivery device to prevent premature precipitation of the liquid embolic. Some embolics use DMSO as the solvent and use it to pre-flush a microcatheter. Again, this pre-flush allows the embolic to pass through the microcatheter without precipitating.

Figure 7:
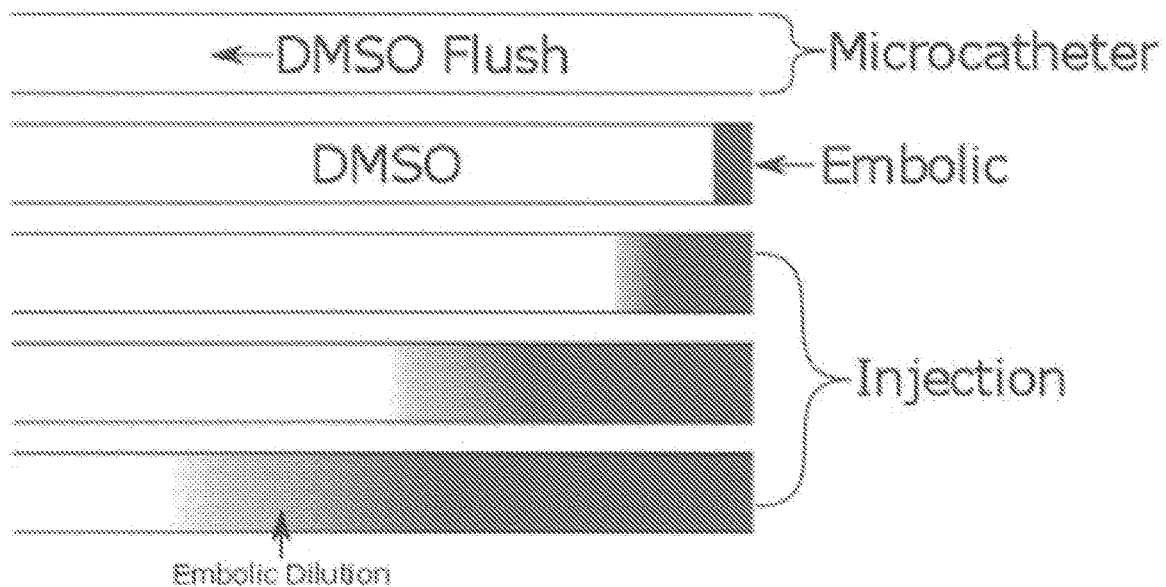
FIG. 7 illustrates a schematic of an embolic dilution using a DMSO microcatheter flush before embolic injection.

Unfortunately, a significant amount of mixing occurs between the flushing agent and the head of the embolic. FIG. 7 illustrates a schematic of how an embolic becomes diluted. As an embolic becomes diluted as it travels down a delivery device (e.g., microcatheter), the diluted embolic becomes less cohesive and is difficult to visualize using fluoroscopy.

In some embodiments, to aid in preventing dilution, a microcatheter is flushed with a mixture of water and solvent. In one embodiment, the co-solvent can be water-DMSO. This co-solvent water-DMSO mixture can slightly solvate the embolic solution but can cause a small semi-precipitated plug or "semi-plug" to form. In embodiments where a semi-plug is desired, this semi-plug may not clog the delivery device.

Figure 8:
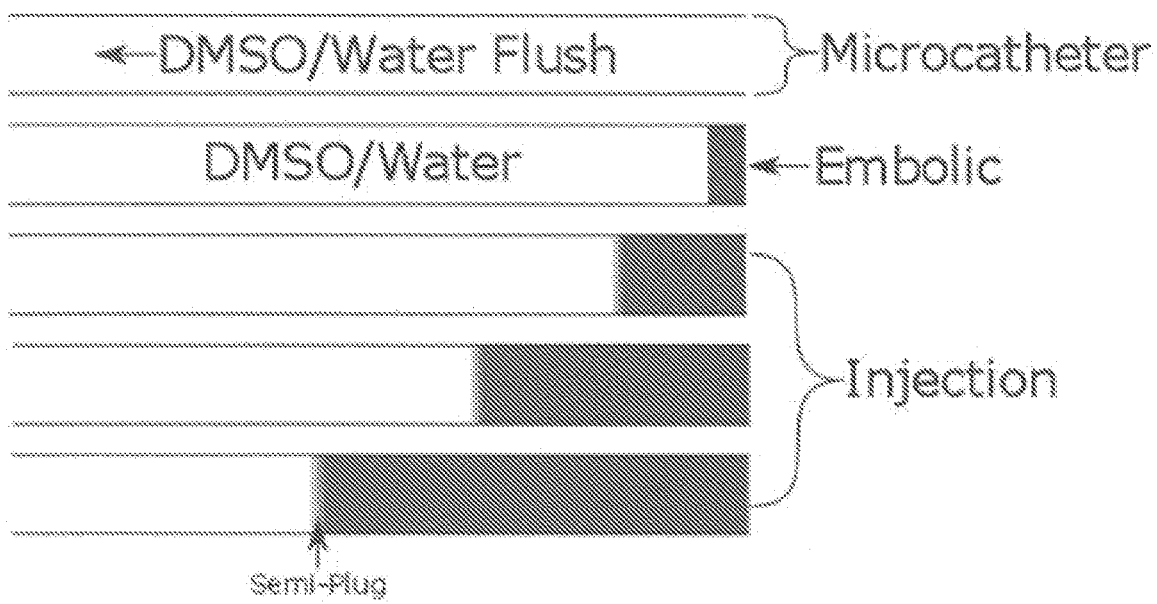
FIG. 8 schematically illustrates DMSO/Water co-solvent microcatheter flush before liquid embolic injection forming a semi-plug.

In other embodiments, the formation of a semi-plug may reduce mixing effects and diffusion of the solvent into the head of the embolic ejection, preventing extensive dilution. FIG. 8 schematically illustrates this idea.

In some embodiments, water:DMSO mixture ratios may range from 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1. In one embodiment, water:DMSO mixture ratios can be about 1-99% water. The water/DMSO mixture can also partially precipitate the liquid embolic therefore a hub adapter must be used with the microcatheter to minimize the volume of the microcatheter hub.

Example 1

Iolhexol and triiodophenol were tested in embolic models under fluoroscopic guidance in conjunction with a lower viscosity precipitating hydrophobic injectable liquid (PHIL 20 wt % in DMSO). Samples were prepared as follows:

| Sample 1 | PHIL 20% w/w | FIG. 2A |
| Sample 2 | PHIL 20% w/w + iohexol 30% w/w | FIG. 2B |
| Sample 3 | PHIL 20% w/w + triiodophenol 30% w/w | FIG. 2C |

To simulate the attenuation of a human body, six inches of acrylic was used as a phantom. ANSI standards suggest using seven inches to represent the abdomen/lumbar spine. However, as tested, a model composed of a pyrex dish (0.25") and a PHIL test block (0.75") added to the attenuation (FIG. 1).

Typical low resolution fluoroscopy was performed to simulate peripheral usage of the embolic (comparison shown in FIG. 2). A dramatic increase in radiopacity is seen for the embolic containing either iohexol or triiodophenol. First, there is greater radiopacity of the embolic in the microcatheter (Headway Duo). Secondly, there is greater radiopacity of the precipitated embolic.

Also, during the investigation, it was not apparent if any of the excipient washed downstream.

Example 2

A monomer of triiodophenol-lactide-co-glycolide acrylate is prepared. The monomer is soluble in DMSO and is radiopaque due to its iodine content. Then, this monomer is dissolved in a PHIL polymer. Experiments demonstrated that 0.2-0.3 gm/ml of PHIL 20% w/w formulation in DMSO increases radiopacity. This procedure is a physical dissolution process and may increase radiopacity without increasing viscosity in an equivalent fashion.

Also, experiments showed that dissolving the monomer in the PHIL polymer also increases the cohesiveness of the embolus.

Some embodiments may require dissolving a short chain polymer in DMSO. An example may be a low viscosity polymer having 15-20% w/w of polymer. Such a short chain polymer can increase radiopacity and increase cohesiveness.

Other embodiments may require dissolving monomer into less radiopaque and less cohesive systems (e.g., 25% w/w, 30% w/w, and 35% w/w PHIL). By dissolving monomer in these formulations, increased radiopacity and cohesiveness may be obtained.

Example 3

Experiment 1: To a container was added 500 mg of acrylamide, 500 mg of polyvinly alcohol (PVA), and 500 mg of poly(4-vinylpyridine) in 4 mL of solution. Then 0.25 mL 1N HCl was added while subjecting to an 80° C. water bath. Then 0.25 mL portions of 1N HCl were added at 1 hr, 3 hr, 3 hr 20 min (temperature of water bath was reduced to 37° C.), 4 hr 10 min, 6 hr 10 min. After the final time point, the solution was left at room temperature over a three-day weekend. After the weekend, the 500 mg of 60 kDA poly(4-vinylpyridine) had dissolved in the solution volume of 5.25 mL. The other polymers did not dissolve.

Example 4

A water-DMSO co-solvent system was evaluated for peripheral compositions of PHIL (PLATO). One iteration of PLATO includes 60% w/w hydroxyethylmethacrylate (HEMA) and 40% w/w triiodophenotriiodophenol-lactide-glycolide (TIP), opposed to PHIL which is 15% HEMA and 85% TIP. The increased amount of HEMA imparted greater cohesiveness, in some circumstances, to the precipitated polymer at the cost of lower radiopacity and higher viscosity. An FDA approved contrast agent is added to augment the radiopacity, however upon addition the viscosity increases (FIG. 5). To counteract the increase in viscosity a reduced amount of PLATO can be used to allow for syringe injection.

To test the implications of this phenomenon, PLATO with 0% water was tested and reduces in viscosity before precipitating as shown in FIG. 6, possibly allowing a liquid embolic to flow more distal. FIG. 6 illustrates that water addition can impact the viscosity of 9 w/w % PLATO containing 30% w/w Iohexol. Water addition (20% w/w) caused the solution to gel and the viscosity was not measured. In contrast, a PLATO formulation with 15% w/w water would not have a reduction in viscosity before precipitation and may lead to more control over the liquid embolic.

HEMA may drive the amount of acceptable water in a co-solvent system. Experimentation shows that PHIL35 can contain up to 5% w/w water before precipitation, thus a higher composition of HEMA appears to drive higher acceptable water concentrations. Furthermore, formulations of PLATO with higher HEMA may also allow more than 15% w/w water before precipitation.

Figure 4:
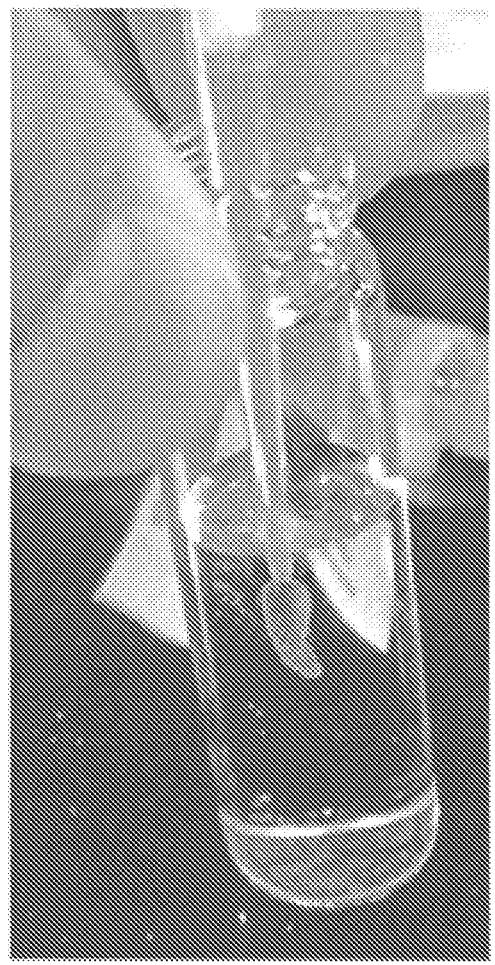
FIG. 4 illustrates a solution of poly(4-vinylpyridine) injected into PBS at pH 7.4.

A 25% w/w solution of poly(4-vinylpyridine) purchased from Sigma Aldrich (472344) was dissolved in water with a final pH of 5.9. Then 50 µL of solution was injected into a vial of 5 mL of 10 mM PBS at pH 7.4. As the polymer was injected the polymer precipitated as illustrated in FIG. 4.

Example 5

Co-Solvent Flush

Figure 9:
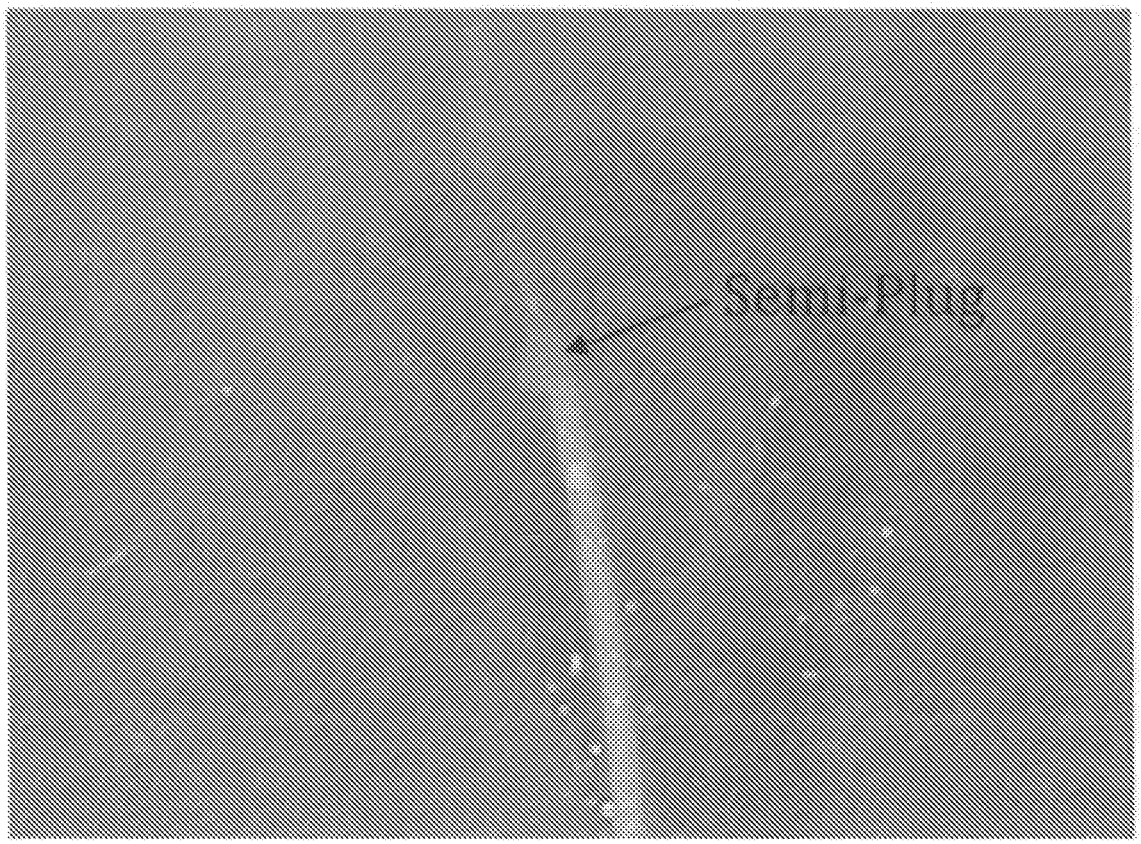
FIG. 9 is a movie still image capture of 9% w/w PLATO injection using a 50/50 water/DMSO flush mixture.

A co-solvent flush was tested with a formulation of the peripheral liquid embolic (PLATO H). A 50/50 water/DMSO mixture was used to flush the catheter before PLATO (9% w/w PLATO, 30% w/w Iohexol, 10% w/w water) was injected into a portal vein model. The first embolic to be ejected from the catheter had greater cohesiveness and minimal washout compared to a neat DMSO flush. FIG. 9 illustrates a still image captured of the first embolic ejection showing the semi-plug preventing dilution.

Unless otherwise indicated, all numbers expressing quantities of ingredients, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing embodiments (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments are described herein, including the best mode known for carrying out the invention. Of course, variations on those preferred embodiments will become apparent to those of ordinary skill in the art upon reading the foregoing description. Those of ordinary skill in the art are expected to employ such variations as appropriate, and embodiments described herein are to be practiced otherwise than specifically described herein. Accordingly, embodiments herein include all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A composition comprising:
a biocompatible polymer;
a solvent; and
a visualization agent;
wherein the biocompatible polymer is soluble in the solvent and insoluble at physiological conditions, and the composition has a viscosity of less than 16 centistokes.

2. The composition of claim 1, wherein the visualization agent is integrated into or associated with the biocompatible polymer.

3. The composition of claim 2, wherein the visualization agent is triiodophenol-lactide-glycolide (TIP).

4. The composition of claim 1, wherein the physiological conditions include contact with a physiological fluid including blood, urine, saliva, mucous, vaginal fluid, seminal fluid, cerebral spinal fluid, sweat, plasma, bile, stomach acid, intestinal fluids, or a combination thereof.

5. The composition of claim 4, wherein the physiological fluid has a pH of about 7.0.

6. The composition of claim 4, wherein the physiological fluid has a pH of between about 7.0 and about 7.8.

7. The composition of claim 1, wherein the solvent is a water miscible organic solvent.

8. The composition of claim 1, wherein the biocompatible polymer comprises an amine and the amine includes an amino group which is about 90% positively charged at a pH of 5 and about 10% positively charged at a pH of 7.

9. The composition of claim 1, wherein the biocompatible polymer includes hydroxyethylmethacrylate (HEMA), lactide, glycolide, polyvinyl pyridine (PVP), 1-vinylimidazole, aminoethyl methacrylate (AEMA), 4-vinylpyridine, alkylalkylacrylate, alkylacrylate, acrylate, styrene, polyvinyl alcohol (PVA), acrylamide, ethylene glycol, or combinations thereof.

10. The composition of claim 1, wherein the biocompatible polymer includes about 60% w/w HEMA and the visualization agent includes about 40% w/w TIP.

11. The composition of claim 1, wherein the biocompatible polymer includes about 15% w/w HEMA and the visualization agent includes about 85% w/w TIP.

12. The composition of claim 1, wherein the solvent is water or a co-solvent of water and dimethyl sulfoxide (DMSO).

13. The composition of claim 1, further comprising aminopropylmethacrylamide.

14. The composition of claim 1, wherein the composition has a viscosity of less than 15 centistokes.

15. The composition of claim 1, wherein the composition has a viscosity of less than 14 centistokes.

16. The composition of claim 1, wherein the biocompatible polymer, together with the visualization agent, forms a cohesive precipitate when insoluble at physiological conditions, and wherein the cohesive precipitate is more cohesive than a precipitate formed from an embolic composition comprising N-butyl-2-cyanoacrylate.

17. The composition of claim 1, wherein the biocompatible polymer is formed from hydroxyethylmethacrylate monomers and aromatic amine monomers.

18. The composition of claim 1, wherein:
the biocompatible polymer comprises about 15% w/w HEMA;
the solvent comprises about 20% w/w DMSO with up to about 5% w/w water; and
the visualization agent comprises about 85% w/w TIP.

19. The composition of claim 1, wherein:
the biocompatible polymer comprises about 60% w/w HEMA;
the solvent comprises about 8% w/w DMSO with up to about 20% w/w water, about 9% w/w DMSO with up to about 15% w/w water, or about 10% w/w DMSO with up to about 15% w/w water; and
the visualization agent comprises about 40% w/w TIP.

20. The composition of claim 1, wherein:
the biocompatible polymer comprises about 50% w/w HEMA;
the solvent comprises about 7% w/w DMSO with up to about 7.0% w/w water, about 7.5% w/w DMSO with up to about 7.5% w/w water, about 8% w/w DMSO with up to about 7.5% w/w water, or about 9% w/w DMSO with up to about 10% w/w water; and
the visualization agent comprises about 50% w/w TIP.

21. The composition of claim 1, wherein:
the biocompatible polymer comprises HEMA;
the solvent comprises a co-solvent of water and DMSO; and
the visualization agent comprises TIP.

22. The composition of claim 1, wherein the composition has a viscosity of less than 13 centistokes.

23. The composition of claim 1, wherein the composition has a viscosity of less than 12 centistokes.

* * * * *